US00PP25005P3

(12) United States Plant Patent
Coiner

(10) Patent No.: US PP25,005 P3
(45) Date of Patent: Oct. 28, 2014

(54) HYBRID TEA ROSE PLANT NAMED 'MOJAVE SUNSET'

(50) Latin Name: *Rosa hybrida*
Varietal Denomination: MOJAVE SUNSET

(76) Inventor: James W. Coiner, Covina, CA (US)

( * ) Notice: Subject to any disclaimer, the term of this patent is extended or adjusted under 35 U.S.C. 154(b) by 102 days.

(21) Appl. No.: 13/573,327

(22) Filed: Sep. 11, 2012

(65) Prior Publication Data

US 2014/0075609 P1 Mar. 13, 2014

(51) Int. Cl.
*A01H 5/00* (2006.01)

(52) U.S. Cl.
USPC ..... Plt./132

(58) Field of Classification Search
USPC ..... Plt./135, 136, 132, 130
See application file for complete search history.

*Primary Examiner* — Kent L Bell
(74) *Attorney, Agent, or Firm* — Christie, Parker & Hale, LLP

(57) ABSTRACT

A new variety of Hybrid Tea rose suitable for garden decoration, having flowers of orange coloration with golden yellow centers.

1 Drawing Sheet

Classification: The present invention relates to a new *Rosa hybrida* plant.

Variety denomination: The new plant has the varietal denomination 'MOJAVE SUNSET'.

BACKGROUND OF THE INVENTION

The present invention relates to a new and distinct Hybrid Tea Rose variety which was originated by crossing as seed and pollen parents two unnamed, undistributed, unpatented seedlings. The varietal denomination of this new rose is 'MOJAVE SUNSET'. Among the novel characteristics possessed by the new variety which distinguish it from other known varieties, are its attractive center petals of golden yellow which transition into orange petals along the edges.

SUMMARY OF THE INVENTION

Among the features which distinguish the new variety from other presently available and commercial rose cultivars known to the inventor is the following combination of characteristics: The plant has a compact upright growing growth habit, suitable for outdoor garden decoration.

Asexual reproduction of the new variety by budding as performed in Kern County Calif., shows that the foregoing and other distinguishing characteristics come true to form and are established and transmitted through succeeding asexual propagations. 'Mojave Sunset' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'Tahitian Sunset' by the following combination of characteristics: similar in coloration but not as intense, softer hues of oranges, yellows, and light pink.

It was found the new variety of hybrid tea rose of the present invention possesses the following characteristics:

A) Unique multi-colored bloom;
B) Exhibits an erect growth habit;
C) Forms attractive green foliage;
D) Exhibits good disease resistance; and
E) Is suitable as garden rose for decoration.

BRIEF DESCRIPTION OF ILLUSTRATION

The accompanying photograph, FIG. 1, illustrates the new variety and shows the flowering thereof from bud to full bloom depicted in color as nearly correct as it is possible to make in a color illustration of the character.

Throughout this specification, color references and/or values are based upon The Colour Chart of The Royal Horticultural Society (1966) except where common terms of color definition are employed.

DESCRIPTION OF THE NEW VARIETY

The following description is of two year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly, with occasional clusters of two to five. Flowers are borne singly, or in irregular rounded clusters on long strong stems, approximately 35 cm to 42 cm in length. Outdoors, the plant blooms nearly continuously during the growing season. The flowers have a slight tea fragrance.

BUD

The peduncle is about 4 cm to about 6 cm in length, of heavy caliper is about 3 cm to about 5 cm in diameter, and usually erect. It is usually smooth, with few stipitate glands, and few hairs and prickles. Peduncle color is near between 145b and 145c.

Before the calyx breaks, the bud is about 1 cm to about 2 cm in diameter at the widest point, about 1.2 cm to about 2.5 cm in length, ovoid in shape with a conspicuous neck. The surface of the bud bears some foliaceous appendages, stipitate glands and glandular bloom with usual observed receptacle diameter of 1 cm. The slender bristle-like foliaceous parts extend beyond the tip of the bud about one-fourth or more of its length. The observed receptacle diameters are between 0.7 cm and 1.2 cm, with the typical diameter of 1 cm. Bud color is near 145b.

The sepals are about 2.8 cm to about 3.2 cm in length and about 1 cm to about 1.5 cm in width at the widest point. The outer surface color of the sepal is near 145b and 145c. The inner surface color of the sepal is near between 137c and 137b. Number of sepals observed ranged between four and five. Typically 5 sepals are observed. The sepals are narrowly ovate to mucronate in shape. Sepal margins are lined with few stipitate glands and hairs with short pointed apex.

The receptacle of the flower is somewhat short in length, about 5 mm to about 7 mm. The receptacle is ovoid in form. The surface is smooth. The receptacle color is near between 145c and 145d.

As the petals open (after the calyx breaks), the bud is about 2 cm to about 2.8 cm in diameter at the widest point, about 3.5 cm to about 4.2 cm in length, and somewhat ovoid in form. The color is close to 39a. As the petal opens the color of the inside surface is close to 39b on the edge, and close to 22b in the center. The color changes at the last centimeter of the base of the petal, to near 21b.

BLOOM

When fully open, the bloom ranges from about 8 cm to about 10 cm in diameter. Petalage is double with about 20 to 27 petals and about 2 to 3 petaloids irregularly arranged. When partially open, the bloom form is somewhat flat to cupped, and the petals are loosely cupped to undulated with petal edges moderately rolled outward. When fully open, the bloom form is somewhat flat to cupped, and the petals are imbricated with petal edges somewhat rolled outward.

PETALS

The substance of the petals is somewhat crisp and of medium thickness, with upper surfaces slightly satiny and under surfaces slightly satiny. The petals are about 4.2 cm to about 6.2 cm in length and about 4.1 cm to about 6.1 cm in width at the widest point. Petal margins are smooth, bearing a slight ruffle.

The outer petals are broadly round to obovate in shape with apexes somewhat rounded, usually slightly notched with one to two notches. The base is slightly thicker with color change to near 21b at the last centimeter of the petal.

The inner petals are broadly round to obovate in shape with apexes somewhat rounded, usually slightly notched with one to two notches. The base is slightly thicker with color change to near 21b at the last centimeter of the petal base.

Petaloids are about 0.5 cm to about 1 cm in length and about 0.4 cm to about 0.8 cm in width at the widest point. Petaloids are shaped round to obovate, with smooth margins and tapering to a narrow base about 2 cm wide. The substance of the petaloids are somewhat crisp and of medium thickness, with upper and under surfaces slightly satiny.

NEWLY OPENED FLOWER

The under surface color of the outer petals is close to 26a and 26b at the base fusing close to 41c and 41d at the apexes.

The upper surface color of the outer petals is close to 26b and 26c at the base gradually changing to 41d at the apexes.

The under surface color of the inner petals is near between 25c and 20c. The upper surface color of the inner petals is near between 25c and 25b.

The under and upper surface color of the petaloids are similar in coloration to the upper and under surfaces of the outer and inner petals.

The general tonality of the newly opened flower is near between 26a and 26b with 41c and 41d at the apexes.

THREE-DAY OLD FLOWER

The under surface color of the outer petals is close to 26a and 26b at the base fusing close to 41c and 41d at the apexes.

The upper surface color of the outer petals is close to 26b and 26c at the base gradually changing to 41d at the apexes.

The under surface color of the inner petals is near between 25c and 20c. The upper surface color of the inner petals is near between 25c and 25b.

The under and upper surface color of the petaloids are similar in coloration to the upper and under surfaces of the outer and inner petal.

On the spent bloom, the petals usually drop off cleanly except for petaloids persist.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids or tucked in the calyx. The filaments are of moderately long length (about 0.5 cm to about 1.3 cm) most with anthers. Filaments are between 13b and 12b in color. The anthers are medium for the class and all open approximately at the same time. Anther color is between 23b and 12c when immature and near between 200a and 167b at maturity. Pollen is abundant and between 17c and 15b in color.

FEMALE REPRODUCTIVE ORGANS

Pistils vary in number (average about 90). The styles are moderately uneven, long in length (about 0.5 cm to about 1.2 cm), somewhat thin in caliper, and moderately separated to loosely bunched. Stigma color is near 13c and 12b. Style color is near 150c and 150d. Ovaries are usually enclosed in the calyx.

Hips have not been observed on this variety when grown in Wasco, Calif.

FOLIAGE

The compound leaves are usually comprised of three to five leaflets and are borne in normal quantities. The five-leaflet leaves are about 12.7 cm to about 15.9 cm in length and about 10.3 cm to about 12.8 cm in width at the widest point, moderately crisp in texture with normal thickness, and semi-glossy in finish. The terminal leaflets are about 5.5 cm to about 8.0 cm in length and about 3.2 cm to about 5 cm in width at the widest point, shaped obovate with obtuse apexes and somewhat round bases. Their margins are serrate.

The upper surface color of the mature leaf is near between 137a and 137b. The under surface color of the mature leaf is near between 145a and 145b. The upper surface color of the young leaf is near between 138a and 138b. The under surface color of the young leaf is near between 145b and 145c.

The rachis is average in caliper and rough, with an observed diameter of 0.1 to 0.2 cm, and typical diameter of 0.1 cm. The observed length of the rachis is between 5-7.6 cm, with typical length of rachis 5.8 cm. The upper side is shallowly grooved with few hairs and stipitate glands and prickles on the edges of the grooves. The underside of the rachis is rough with few hairs and stipitate glands and small to medium prickles. The rachis color is near between 146c and 146b.

The stipules are about 1.2 cm to about 1.4 cm in length and about 1 cm to about 1.5 cm in width with short to medium points that usually turn out at an angle of less than 45 degrees toward the stem. The stipules color is near between 146c and 146b. The stipules appear in pairs, with a thin leaf-like appendage that is near 0.2 cm wide attached to the base of the petiole from the tip of the stipule down. Observed length of stipule is between 0.5 cm and 1.2 cm. Typical length of stipule is 1.5 cm.

The petiole is average in caliper and rough. The upper side is deeply to moderately grooved with many hairs and stipitate glands and prickles on the edges of the grooves. The petiole color is near between 146b and 146c. The observed petiole length ranges between 0.1 cm to 1.5 cm, with the typical petiole length of 0.2 cm from the side leaflets of the compound leaf to the stipule, and the typical petiole length from the top leaflet of the compound leaf to the end stipule of 1.2 cm.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a compact upright medium height growth habit of about 110 cm to about 125 cm in height and about 60 cm to about 40 cm spread at the widest point, with full branching. It displays vigorous growth and the canes are of medium caliper for the class.

The color of the major stems is near between 148a and 146a. They bear large prickles that are about 0.07 cm to about 1.1 cm in length. The large prickles are almost straight and hooked slightly downward with medium length to rounded base; prickle color is near 166d. The major stem bears few small prickles of similar shape and coloration. There are few fine coarse hairs of similar shape and coloration which are near between 166c and 166d.

The color of the branches is near between 148a and 146b. They bear few large prickles which are of similar size and shape to the large prickles on the major stems; prickle color is near 166c. The branches bear several small prickles of similar shape and coloration and which are near 166c.

The color of the new shoots is near between 144a and 148b. They bear several large prickles which are of similar size and shape to the large prickles on the major stems; prickle color is near 166c.

I claim:

1. A new and distinct Hybrid Tea rose plant of the variety substantially as described and illustrated herein.

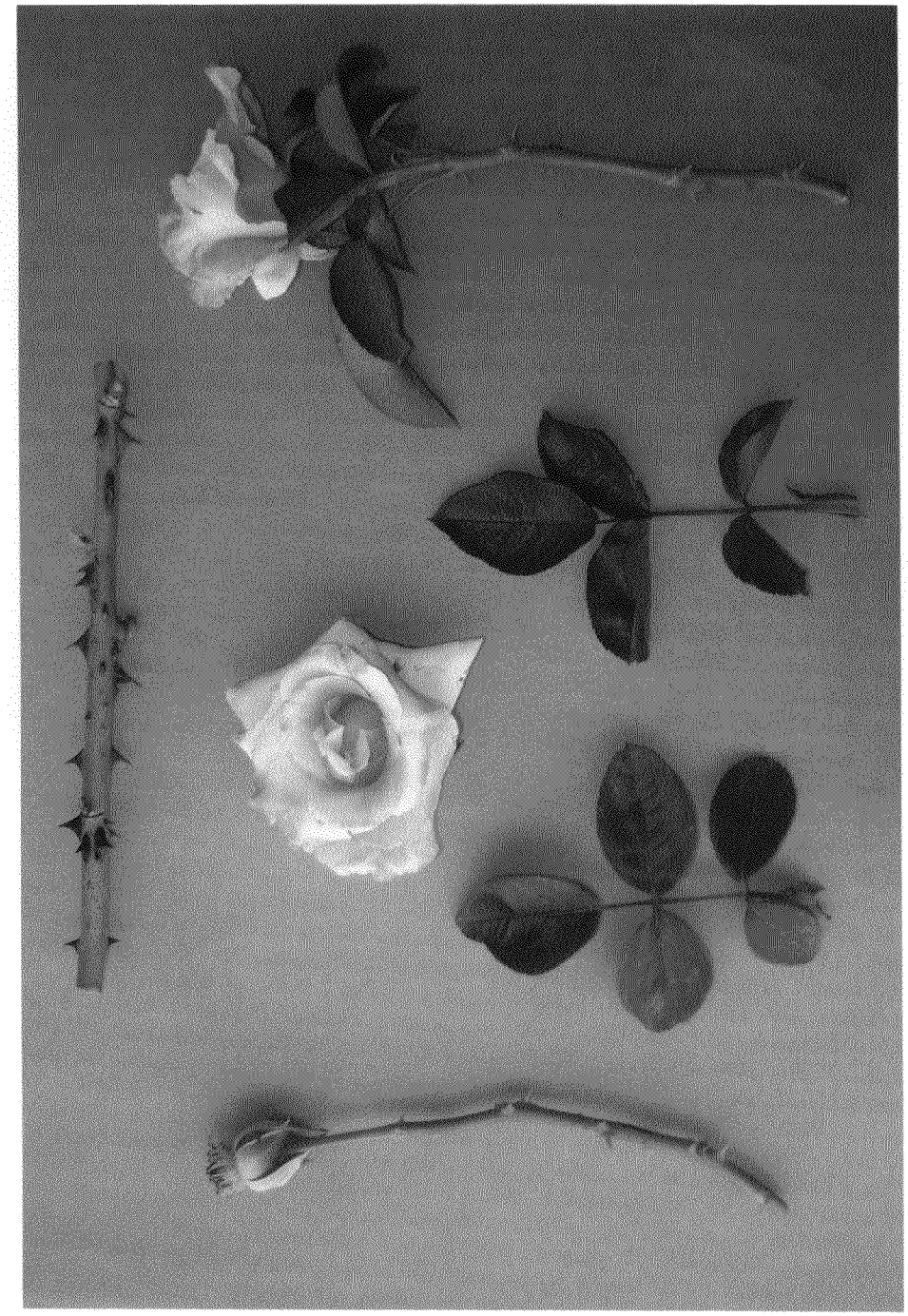

* * * * *